(12) United States Patent
Linnau et al.

(10) Patent No.: US 6,605,222 B1
(45) Date of Patent: Aug. 12, 2003

(54) METHOD FOR PRODUCING A FACTOR VIII/VON WILLEBRAND FACTOR COMPLEX

(75) Inventors: Yendra Linnau, Vienna (AT); Wolfgang Schoenhofer, St. Poelten (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/623,245

(22) PCT Filed: Feb. 25, 1999

(86) PCT No.: PCT/AT99/00048
§ 371 (c)(1),
(2), (4) Date: Mar. 19, 2001

(87) PCT Pub. No.: WO99/43712
PCT Pub. Date: Sep. 2, 1999

(30) Foreign Application Priority Data

May 20, 1998 (AT) ............................................. A866/98

(51) Int. Cl.$^7$ ............................................. B01D 15/08
(52) U.S. Cl. .................. 210/635; 210/656; 530/383; 530/416
(58) Field of Search ................. 210/635, 656, 210/659, 198.2; 530/383, 416

(56) References Cited

U.S. PATENT DOCUMENTS

| 5,096,593 A | * | 3/1992 | Wakita | ...................... 210/656 |
|---|---|---|---|---|
| 5,278,289 A | * | 1/1994 | Johnson | ...................... 530/383 |
| 5,831,026 A | * | 11/1998 | Almstedt | ...................... 530/383 |
| 6,005,077 A | * | 12/1999 | Schwarz | ...................... 530/383 |
| 6,037,452 A | * | 3/2000 | Minamino | ...................... 530/383 |
| 6,143,179 A | * | 11/2000 | Muller | ...................... 210/635 |
| 6,239,261 B1 | * | 5/2001 | Heimburger | ...................... 530/380 |
| 6,307,032 B1 | * | 10/2001 | Schonhofer | ...................... 530/413 |

FOREIGN PATENT DOCUMENTS

| EP | 295 645 | * | 12/1988 | ................. 210/656 |
|---|---|---|---|---|
| EP | 600 480 | * | 6/1994 | ................. 210/656 |
| WO | WO 91/13093 | * | 9/1991 | ................. 210/656 |
| WO | WO 93/15199 | * | 1/1993 | ................. 210/656 |
| WO | WO 97/34930 | * | 9/1997 | ................. 210/656 |
| WO | WO 97/39033 | * | 10/1997 | ................. 210/656 |
| WO | WO 98/38219 | * | 9/1998 | ................. 210/656 |

* cited by examiner

Primary Examiner—Ernest G. Therkorn
(74) Attorney, Agent, or Firm—Townsend and Townsend and Crew LLP; Michael F. Fedrick

(57) ABSTRACT

The invention relates to a method for the production of factor VIII:C/von Willebrand factor complex from plasma or a plasma fraction by chromatography in a cation exchanger, wherein the factor VIII:C/von Willebrand factor complex is obtained with at least 300 times the purity of the plasma and the yield of factor VIII:C and the von Willebrand factor is at least 50% in relation to cryoprecipitates or analogous plasma fractions.

9 Claims, No Drawings

METHOD FOR PRODUCING A FACTOR VIII/VON WILLEBRAND FACTOR COMPLEX

REFERENCE TO RELATED APPLICATIONS

This application is a 371 of PCT/AT99/00048 filed Feb. 25, 1999.

The invention concerns a method for producing and purification of factor VIII:C/vWF complex from plasma or a plasma fraction by chromatography on a cation exchanger.

Factor VIII preparations have been used for more than 30 years for treatment of hemophilia diseases. The factor VIII:C/vWF, complex consists of two molecules, the antihemophilic factor (factor VIII:C) and the von Willebrand factor (vWF). Both proteins are under the control of various genes, but they circulate in the plasma as a noncovalently bonded complex (factor VIII:C/vWF complex).

Antihemophilic factor is a glycoprotein that is defective or missing in people with hemophilia A. The von Willebrand factor (wWF) is a multimeric glycoprotein, which is present in reduced amounts, or is qualitatively abnormal in patients with von Willebrand's disease. The plasma concentration of VIII:C is approximately between 100 and 200 ng/ml, while the concentration of vWF is roughly 10 µg/ml.

Preparation of a pharmaceutically compatible FVIII:C/vWF complex should be aimed at making available a product that is stable and, above all, free of undesirable accompanying proteins. Any unnoticed protein load brings the risk of undesirable side effects.

Various chromatographic methods for obtaining factor VIII:C/vWF complex have been described in the prior art, for example by anion exchange, chromatography, hydrophobic interaction chromatography or affinity chromatography.

One method for obtaining factor VIII:C/vWF complex from human plasma using cation exchange chromatography is known from EP-0 600 480. In this method several steps are carried out for purification, including two chromatographic purifications on an anion exchanger, with the cation exchange chromatography being carried out at the end. Considerable losses of activity occur in the multistep purification.

U.S. Pat. No. 5,278,289 describes a method for producing purified and stabilized factor VIII from a biological sample. In this method the.biological sample was applied to a cation exchanger column, but only an incompletely purified protein was obtained. Complete purification is only achieved by means of the subsequently connected anion exchanger column. The product contains FVIII:C, which was obtained through dissociation of the factor VIII:C/vWF complex.

The task of this invention is to make available the factor VIII:C/vWF complex or a factor VIII:C/vWF complex preparation in high purity and at the same time with high yield via a simple chromatographic process. This task is solved in accordance with the invention by a preparation method using cation exchange chromatography for adsorption and purification of plasma factor VIII:C/vWF complex on a cation exchanger, where the factor VIII:C/vWF complex is obtained with a purity of at least 300-fold with respect to the plasma and a yield of at least 50% of the FVIII:C and vWF, compared to the cryoprecipitate or analogous plasma fractions.

Preferably, commercially available cation exchanger materials with carboxy or sulfhydro groups are used as cation exchange materials. S- or DM-Sepharose (Amersham Pharmacia), Fractogel EMD-$SO_3^-$ or $COO^-$ (Merck, Darmstadt) or SP- or CM-Toyopearl (Tosohaas) can preferably be used.

Plasma or a plasma fraction can be used as the starting material. For example, a cryoprecipitate can be used as a plasma fraction, possibly after prior adsorption treatment to remove prothrombin complex factors, or an analogous plasma fraction can be used, for example a Cohn fraction like Cohn I, or a corresponding fraction in accordance with Pool et al. (New England Journal of Medicine 273, 1443–1447) can be used. Optionally, fibrinogen can be removed by precipitation.

Preferably, the starting material is dissolved in a buffer that contains calcium ions. The buffer can also contain a detergent. The ionic strength of the adsorption buffer is generally 0–10 mS, 6–8 mS. If the adsorbed FVIII:C/vWF complex is washed, this washing is preferably carried out with a washing buffer that has an ionic strength over that of the adsorption buffer. The elution of the factor VIII:C/vWF complex, which preferably has not been fractionated, is achieved through this increase of the ionic strength. The ionic strength of the elution buffer is usually 10–100 mS, preferably 25–60 mS. Acetate buffers, citrate buffers or histidine-containing buffers, for example, can be used as elution buffers. Preferably a sodium chloride-containing elution buffer is used. The pH should kept approximately neutral during the purification, for example in a range of 6–8.

In order to prevent any dissociation of the factor VIII:C/vWF complex during the chromatographic purification a buffer with a calcium ion concentration of, for example, 0.5–10 mM is preferably used.

In order to avoid the risk of the transmission of human pathogenic infectious agents, including viruses transmitted by blood such as HIV and hepatitis viruses, for example HAV, HBV, HCV, HGV and parvo viruses, and also the infectious causative agents of BSE and CJD, a number of measures can be carried out. The factor VIII:C/vWF complex can be subjected to a process for inactivation or depletion, stripping of the human pathogens before or after the chromatographic purification. Methods using virucidal chemical substances can be carried, out preferably before or during the chromatographic purification process, and as a result the virucidal agent can be efficiently removed at the same time as the purification of the factor VIII:C/vWF complex. Preferably at least two measures that bring about inactivation or depletion of the viruses by means of a different mechanism are carried out. These include chemical, chemical-physical and physical methods.

Among effective measures for inactivation of viruses are, for example, treatment with organic solvents and/or detergents (EP-0 131 740, EP-0 050 061), treatment with chaotropic agents (EP-0 431 129), heat treatment methods, preferably in lyophilized dry or wet state, as described in EP-0 159 311, combination methods such as that of EP-0 519 901 and physical methods. The latter caused inactivation of viruses, for example, by means of light, for instance in the presence of photosensitizers (EP-0 471 794 or WO 97/37686).

The methods of removal of human pathogens include in particular filtration using ultrafilters, deep bed filters or nanofilters (A 341/98). However, precipitation steps or other protein purification measures such as adsorption also contribute to removal of pathogens that may be present.

The method in accordance with the invention is excellently suitable for purification of the factor VIII:C/vWF complex from a plasma fraction on an industrial scale, since due to the efficient one-step purification a large number of additional purification steps such as, for example, additional chromatographic purification steps, are not necessary. It is in particular in the large scale production of biological preparations that a simple one step method like the method in accordance with the invention, in which such high yields and such purity can be achieved, is particularly desirable.

Surprisingly, it turned out that the factor VIII:C/vWF complex can be produced by simple cation exchange chromatography with an at least 300-fold purity over the plasma, preferably at least 400-fold purity, with a simultaneously high yield of FVIII:C and vWF of at least 50%, preferably at least 60%, most preferably at least 70%, with respect to the cryoprecipitate or similar plasma fraction. It is additionally preferred to set up the purification process so that only one single chromatographic purification is carried out, mainly that on the cation exchanger.

It turned out that a yield of factor VIII:C/vWF complex of more than 90% with respect to the activity before chromatography can be obtained. As a result, even during the chromatographic purification the usual stabilizers of the factor VIII:C/vWF complex such as antithrombin III and/or heparin can be avoided without the threat of considerable losses due to denaturation.

The activity of the factor VIII:C or vWF is affected very little by cation exchange chromatography. The factor VIII:C activity can be determined, for example, by means of chromogenic assay (immunochrome FVIII:C, Immuno AG). The activity of vWF can be determined by a collagen binding test following Thomas et al. (Haemostaseologie, 14, 133–319 (1994)) or by means of ELISA.

For formulation of a pharmaceutical factor VIII:C/vWF complex preparation, it is usually diafiltered and sterilefiltered as well as optionally lypphilized.

The invention is illustrated in more detail by means of the following example.

EXAMPLE 1

Isolation of the FVIII:C/vWF complex via cation exchange.

Example 1A 210 g cryoprecipitate is dissolved in 950 ml $CaCl_2$ heparin-containing citrate buffer and adjusted to pH 6.0. Insoluble fractions, mainly fibrinogen, were removed. For inactivation of pathogenic viruses that were possibly present the clear solution was treated with 1% Triton X100 and 0.3% TNBP (tri-(n-butyl) phosphate). 100 ml Fractogel EMD-$SO_3^-$-650(M) (Merck, Darmstadt (DE)) was used for adsorption of the virus-inactivated FVIII, which was equilibrated beforehand at pH 6.0 in an acetate-buffered NaCl solution with conductivity of 10 mS/cm. The FVIII was eluted from the gel by increasing the ionic strength to 500 mM NaCl; first washing with 500 mL 150 mM NaCl solution was carried out.

Example 1B

Toyopearl SP-550C was used instead of Fractogel EMD-$SO_3^-$ in this example.

Results

| | Yield/Plasma FVIII:C | vWF | Degree of Purity Compared to Plasma |
|---|---|---|---|
| Example 1A | 62% | 68% | 450 X |
| Example 1B | 56% | 62% | 370 X |

FVIII:C and vWF were obtained in the same fraction.

What is claimed:

1. A method for producing a preparation containing factor VIII:C/vWF complex, said method comprising:
   treating a starting material containing a factor VIII:C/vWF complex, wherein the starting material is selected from the group consisting of plasma and a plasma fraction, with a cation exchanger, where the factor VIII:C/vWF complex is bonded to the cation exchanger;
   separating unbonded starting material; and
   eluting the factor VIII:C/vWF complex from the cation exchanger, wherein chromatography on the cation exchanger is the only chromatographic purification.

2. A method as in claim 1, wherein the chromatography is in the presence of virucidal substances.

3. A method as in claim 2 wherein the factor VIII:C/vWF complex is eluted in one step.

4. A method as in claim 1, wherein the factor VIII:C/vWF complex is eluted in one step.

5. A method as in claim 1, wherein the plasma fraction is a Cohn fraction.

6. The method as in claim 1, wherein the plasma fraction is a cryoprecipitate.

7. The method as in claim 6, wherein the factor VIII:C/vWF complex has a yield of at least 50% of the factor VIII:C/vWF in the cryoprecipitate.

8. A method as in claim 1, wherein the factor VIII:C/vWF complex has at least 370-fold increased purity compared to plasma.

9. A method as in claim 1, wherein the factor VIII:C/vWF complex has a yield of at least 50% of the factor VIII:C/vWF in the plasma fraction.

* * * * *